United States Patent
Shie et al.

(10) Patent No.: US 8,198,284 B2
(45) Date of Patent: Jun. 12, 2012

(54) TREATMENT OF NEURODEGENERATIVE DISORDERS WITH THIOUREA COMPOUNDS

(75) Inventors: Feng-Shiun Shie, Hsin-Chu (TW); Jyh-Haur Chern, Taipei (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 127 days.

(21) Appl. No.: 12/410,136

(22) Filed: Mar. 24, 2009

(65) Prior Publication Data

US 2009/0275596 A1    Nov. 5, 2009

Related U.S. Application Data

(60) Provisional application No. 61/049,052, filed on Apr. 30, 2008.

(51) Int. Cl.
| A61K 31/17 | (2006.01) |
|---|---|
| A61K 31/4965 | (2006.01) |
| A61K 31/404 | (2006.01) |
| A61P 25/00 | (2006.01) |
| A61P 25/16 | (2006.01) |
| A61P 25/28 | (2006.01) |

(52) U.S. Cl. .............. 514/255.03; 514/587; 514/586; 514/514

(58) Field of Classification Search .......... 514/255.03, 514/587, 586, 415
See application file for complete search history.

(56) References Cited

U.S. PATENT DOCUMENTS

| 3,890,348 | A | 6/1975 | Kathawala |
|---|---|---|---|
| 4,221,817 | A | 9/1980 | Tenne |
| 4,413,006 | A | 11/1983 | Kanno et al. |
| 4,574,124 | A | 3/1986 | Kabbe et al. |
| 5,932,742 | A | 8/1999 | Yoon et al. |
| 6,696,487 | B2 | 2/2004 | Gerusz et al. |
| 6,706,751 | B2 | 3/2004 | Aebi et al. |
| 7,094,807 | B2 | 8/2006 | Chen et al. |
| 7,102,007 | B2 | 9/2006 | Aebi et al. |
| 2005/0020624 | A1 | 1/2005 | Aebi et al. |
| 2005/0032849 | A1 | 2/2005 | Phadke et al. |
| 2005/0228013 | A1 | 10/2005 | Thurkauf et al. |
| 2006/0025416 | A1 | 2/2006 | Phadke et al. |
| 2008/0306090 | A1* | 12/2008 | Chern et al. ............. 514/255.04 |
| 2009/0264404 | A1 | 10/2009 | Yamashita et al. |

FOREIGN PATENT DOCUMENTS

| DE | 2040438 | 3/1971 |
|---|---|---|
| FR | 2447378 | 1/1979 |
| GB | 1332008 | 10/1973 |
| GB | 2056968 | 3/1981 |
| JP | 2005330284 | 2/2005 |
| JP | 2005/144790 | 5/2005 |
| WO | WO 99/40088 | 8/1999 |
| WO | WO2004/046095 | 6/2004 |
| WO | WO2004/096210 | 11/2004 |
| WO | WO2005/095345 | 10/2005 |
| WO | WO2006/122011 | 11/2006 |

OTHER PUBLICATIONS

Chern et al (U.S. Publication 2008/0306090 with a filing date of Jun. 8, 2007) and Perry (Cognitive Dysfunction in Chronic Hepatitic C: A review, Dig Dis Sci (2008) 53: p. 307-321, published online: Aug. 17, 2007).*
Bosboom (Cognitive dysfunction and dementia in Parkinson's disease, Journal of Neural Transm (2004) 111: pp. 1303-1315).*
Lee et al. (Journal of Pharmacology and Experimental Therapeutics, 2007, 321, 823-29).*
Cory et al., "Use of an Aqueous Soluble Tetrazolium/Formazan Assay for Cell Growth Assays in Culture," *Cancer Communications*, vol. 3, No. 7, (1991).
Honda et al., Chem. Abst. 135 357776 (2001).
Willson et al. Chem. Abst. 118: 212577 (1993).
Bennett et al., J. Am Chem Soc. 1953 75(23); 6039-6040.
Gugliamelli, Luis et al., Anales de la Asociacion Quimica Argentina (1927), 15, pp. 337-362.
Arafa, Reem et al., J. Med. Chem. 2005, 48, 5480-5488.
Document No. 142:56122, retrieved from CAPLUS on Jan. 6, 2010.
Document No. 140:209908, retrieved from CAPLUS on Jan. 6, 2010.
Document No. 86:55235, retrieved from CAPLUS on Jan. 6, 2010.
Document No. 140:406359, retrieved from CAPLUS on Jan. 6, 2010.
Document No. 143:163157, retrieved from CAPLUS on Jan. 6, 2010.
Document No. 139:69296, retrieved from CAPLUS on Jan. 6, 2010.
Document No. 132:279477, retrieved from CAPLUS on Jan. 6, 2010.

* cited by examiner

*Primary Examiner* — San-Ming Hui
*Assistant Examiner* — Kathrien Cruz
(74) *Attorney, Agent, or Firm* — Occhiuti Rohlicek & Tsao LLP

(57) ABSTRACT

A method for treating a neurodegenerative disorder. The method includes administering to a subject in need thereof an effective amount of one or more thiourea compounds of formula (I) or (II):

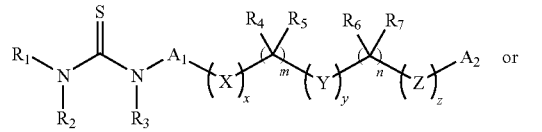

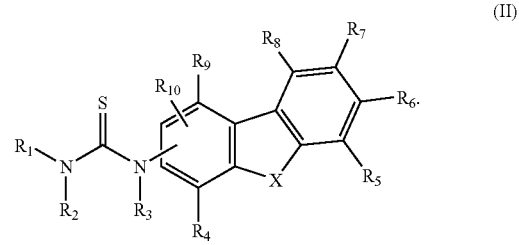

Each variable in formula (I) or (II) is defined herein. Also disclosed is use of these thiourea compounds to reduce microglia-mediated neuro-inflammation or enhancing microglial phagocytosis of Aβ.

2 Claims, No Drawings

TREATMENT OF NEURODEGENERATIVE DISORDERS WITH THIOUREA COMPOUNDS

CROSS REFERENCE TO RELATED APPLICATIONS

This application claims priority to U.S. Provisional Application Ser. No. 61/049,052 filed Apr. 30, 2008, the content of which is hereby incorporated by reference in its entirety.

BACKGROUND

Neurodegenerative diseases afflict more than 30 million of individuals worldwide. Current therapies target the symptoms of these diseases, generally with only modest efficacy.

Alzheimer's disease (AD), the most prevalent neurodegenerative disease, is characterized clinically by progressive memory loss and cognitive dysfunction, and pathologically by the development in the brain of intracellular neurofibrillary tangles containing abnormally hyperphosphorylated tau and extracellular senile amyloid plaques constituted predominantly of β-amyloid (Aβ).

Recently, microglia, the resident immune cells of brain, have been considered to play an important role in the pathogenesis of neurodegenerative diseases, more specifically, microglia-mediated neuro-inflammation where microglia are activated has been implicated in the development of these diseases especially in AD and Parkinson's disease (PD). However, microglial activation is associated with production of an assortment of effector molecules that may have complex and mixed effects on Aβ clearance and neuronal survival. Also, based on recent studies, complete inhibition of microglial activation using non-steroidal anti-inflammatory drugs appears to show limited therapeutic benefits for the diseases. See e.g., Shie et al., *Current Medicinal Chemistry*, 2007 (14): 2865-2871; Hayden, et. al., *Neurology*, 2007 (69):275-282; Britschgi et al., *Nat. Med.*, 2007 (13):408-4099; Shie et al., *Brain Pathol.*, 2005 (15):134-138; Jin et al., *Journal of Neuroinflammation*, 2007 (4):2-11; and Gao et al., *FASEB J.*, 2003 (17): 1957-1959.

Fine-tuning microglial activation may confer better means for the therapy. There is growing consensus that a favorable combination of reduced microglia-mediated neuro-inflammation and enhanced phagocytic activity of microglia is essential in slowing the progression of the neurodegenerative diseases.

SUMMARY

The present invention is based on an unexpected discovery that certain thiourea compounds are effective in both reducing microglia-mediated neuro-inflammation and enhancing phagocytosis of Aβ, which allows these compounds to be applied in treating neurodegenerative diseases, e.g., AD.

In one aspect, this invention features treating a neurodegenerative disorder by administering to a subject in need of the treatment an effective amount of a thiourea compound of formula (I):

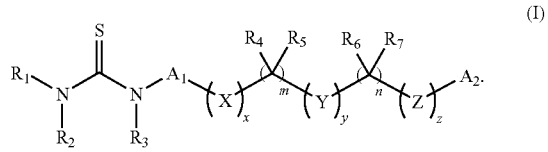

(I)

In this formula, $A_1$ is arylene or heteroarylene; $A_2$ is aryl, heteroaryl, H, alkyl, alkenyl, alkynyl, cycloalkyl, cycloalkenyl, heterocycloalkyl, heterocycloalkenyl, or $C(O)R_a$, in which $R_a$ is alkyl, alkenyl, alkynyl, cycloalkyl, cycloalkenyl, heterocycloalkyl, heterocycloalkenyl, aryl, or heteroaryl; each of $R_1$, $R_2$, and $R_3$, independently, is H, alkyl, alkenyl, alkynyl, cycloalkyl, cycloalkenyl, heterocycloalkyl, heterocycloalkenyl, aryl, heteroaryl, or $C(O)R_b$, in which $R_b$ is alkyl, alkenyl, alkynyl, cycloalkyl, cycloalkenyl, heterocycloalkyl, heterocycloalkenyl, aryl, or heteroaryl; or $R_1$ and $R_2$, together with the nitrogen atom to which they are bonded, are heterocycloalkyl; or $R_2$ and $R_3$, together with the two nitrogen atoms to which they are bonded and the carbon atom bonded to both of the two nitrogen atoms, are heterocycloalkyl; or $R_3$, the nitrogen atom to which it is bonded, and the ring atom of $A_1$ to which the nitrogen atom is bonded, together with another ring atom of $A_1$, are heterocycloalkyl or heterocycloalkenyl that is fused with $A_1$; each of $R_4$, $R_5$, $R_6$, and $R_7$, independently, is H, halo, nitro, cyano, amino, hydroxy, alkoxy, aryloxy, alkyl, alkenyl, alkynyl, cycloalkyl, cycloalkenyl, heterocycloalkyl, aryl, or heteroaryl; each of X, Y, and Z, independently, is O, S, SO, $SO_2$, $N(R_c)$, $C(O)$, $C(O)O$, $C(O)NR_c$, $NR_cC(O)NR_d$, $NR_cC(S)NR_d$, $NR_cC(O)O$, $SO_2NR_c$, alkylene, alkenylene, alkynylene, cycloalkylene, cycloalkenylene, heterocycloalkylene, heterocycloalkenylene, arylene, or heteroarylene, in which each of $R_c$ and $R_d$, independently, is H, alkyl, cycloalkyl, heterocycloalkyl, aryl, or heteroaryl; each of m and n, independently, is 0, 1, 2, 3, 4, 5, 6, or 7; and each of x, y, and z, independently, is 0 or 1.

In particular, this invention features a method for treating Alzheimer's disease or Parkinson's disease, by administering to a subject in need thereof an effective amount of a compound of formula (I) shown above. Referring to formula (I), a subset of the just-described compounds are those in which X is O and x is 1. In these compounds, $A_1$ can be 1,3-phenylene or 1,4-phenylene; Z can be $NHSO_2$, NHC(O), C(O)NH, NHC(O)O, NHC(O)NH, NHC(S)NH, NHC(=NH)NH, cycloalkylene, or heterocycloalkylene (e.g.,

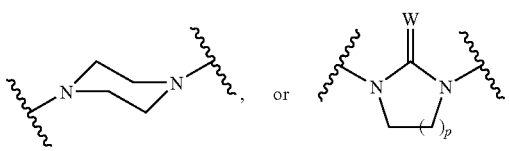

in which W is O or S and p is 1, 2, or 3); z can be 1; y can be 0; $A_2$ can be phenyl, pyridyl, or naphthyl, each of which is optionally substituted with halo, alkoxy, aryloxy, alkyl, cycloalkyl, aryl, or heteroaryl; each of $R_1$, $R_2$, and $R_3$ can be H; each of $R_4$, $R_5$, $R_6$, and $R_7$ can be H; and each of m and n, independently, can be 0, 1, 2, 3, 4, or 5; or Z can be NHC(S)

NH and $A_2$ can be naphthyl optionally substituted with halo, alkoxy, aryloxy, alkyl, cycloalkyl, aryl, or heteroaryl.

Another subset of the compounds of formula (I) includes those in which $R_3$ and the nitrogen atom to which it is bonded, together with $A_1$, are

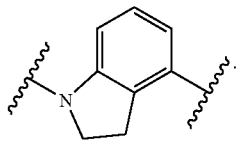

In these compounds, $R_1$ can be H and $R_2$ can be alkyl or $C(O)R_b$; X can be O and x can be 1; Z can be O, z can be 0 or 1, and y can be 0; $A_2$ can be aryl or heteroaryl; each of $R_4$, $R_5$, $R_6$, and $R_7$ can be H; and each of m and n, independently, can be 0, 1, 2, 3, 4, or 5; or $R_2$ can be alkyl and each of x, y, z can be 0.

Still another subset of the compounds of formula (I) includes those in which Z is O and z is 1. In these compounds, $A_2$ can be aryl (e.g., phenyl optionally substituted with arylamino, halo, alkoxy, aryloxy, alkyl, cycloalkyl, aryl, or heteroaryl) or heteroaryl; each of $R_1$, $R_2$, and $R_3$ can be H; or each of $R_4$, $R_5$, $R_6$, and $R_7$ can be H and each of m and n, independently, can be 0, 1, 2, 3, 4, or 5.

The term "treating" or "treatment" refers to administering one or more thiourea compounds to a subject, who has a neurodegenerative disorder, a symptom of or a predisposition toward such a disorder, with the purpose to confer a therapeutic effect, e.g., to cure, relieve, alter, affect, ameliorate, or prevent the disorder, the symptom of or the predisposition toward it. Such a subject can be identified by a health care professional based on results from any suitable diagnostic method. "An effective amount" refers to the amount of one or more active thiourea compounds that is required to confer a therapeutic effect on a treated subject.

In another aspect, this invention features treating a neurodegenerative disorder by administering to a subject in need of the treatment an effective amount of a thiourea compound of formula (II):

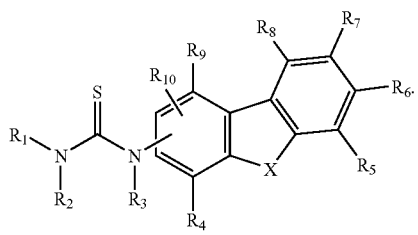

(II)

In this formula, X is O, $N(R_a)$, $C(R_aR_b)$, or $C(O)$; in which each of $R_a$ and $R_b$, independently, is H, alkyl, cycloalkyl, heterocycloalkyl, aryl, or heteroaryl; each of $R_1$, $R_2$, and $R_3$, independently, is H, alkyl, alkenyl, alkynyl, cycloalkyl, cycloalkenyl, heterocycloalkyl, heterocycloalkenyl, aryl, or heteroaryl; or $R_2$ and $R_3$, together with the two nitrogen atoms to which they are bonded and the carbon atom bonded to both of the two nitrogen atoms, are heterocycloalkyl; and each of $R_4$, $R_5$, $R_6$, $R_7$, $R_8$, $R_9$, and $R_{10}$, independently, is H, alkyl, alkenyl, alkynyl, cycloalkyl, cycloalkenyl, heterocycloalkyl, heterocycloalkenyl, aryl, heteroaryl, halo, $N(R_cR_d)$, $N(R_c)$—$C(S)$—$N(R_dR_e)$; $N(R_c)$—$C(O)R_d$, or $N(R_c)$—$C(O)O$—$R_d$;

in which each of $R_c$, $R_d$, and $R_e$, independently, is H, alkyl, cycloalkyl, heterocycloalkyl, aryl, or heteroaryl; provided that if $R_{10}$ is at the 3-position, then

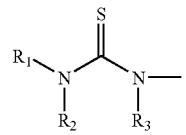

is at the 4-position; and if $R_{10}$ is at the 4-position, then

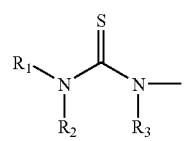

is at the 3-position.

In particular, this invention features a method for treating AD or PD by administering to a subject in need thereof an effective amount of a compound of formula (II) shown above. For example, one can administer to a subject having a neurodegenerative disorder a thiourea compound of formula (II), in which the compound has the following formula:

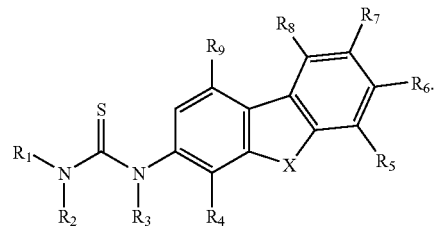

In this formula, X, $R_1$, $R_2$, $R_3$, $R_4$, $R_5$, $R_6$, $R_7$, $R_8$, and $R_9$ are as defined immediately above.

A subject in need of treatment of a neurodegenerative disorder can also be concurrently administered with a thiourea compound of the above formulae and one or more other therapeutic agents. Examples of such therapeutic agents may include tacrine, donepezil, galantamine, and rivastigmine, and memantine. The term "concurrently administered" refers to administering a thiourea compound and one or more other therapeutic agents at the same time or at different times during a treatment period.

In still another aspect, this invention features a method of reducing microglia-mediated neuro-inflammation and/or enhancing microglial phagocytosis of Aβ by administering to a subject in need an effective amount of one or more thiourea compounds of the above formula (I) or (II). A subject in need can be a patient having a neurodegenerative disorder, e.g., AD or PD.

The term "alkyl" refers to a straight or branched monovalent hydrocarbon containing 1-20 carbon atoms (e.g., $C_1$-$C_{10}$). Examples of alkyl include, but are not limited to, methyl, ethyl, n-propyl, i-propyl, n-butyl, i-butyl, and t-butyl. The term "alkylene" refers to a straight or branched bivalent hydrocarbon, containing 1-20 carbon atoms (e.g., $C_1$-$C_{10}$). Examples of alkylene include, but are not limited to, methylene and ethylene. The terms "alkenyl" and "alkenylene" respectively refer to a straight or branched monovalent and bivalent hydrocarbon containing 2-20 carbon atoms (e.g., $C_2$-$C_{10}$) and one or more double bonds. Examples of alkenyl and alkenylene include, but are not limited to, ethenyl, propenyl, propenylene, allyl, and 1,4-butadienyl. The terms "alkynyl" and "alkynylene" respectively refer to a straight or branched monovalent and bivalent hydrocarbon containing 2-20 carbon atoms (e.g., $C_2$-$C_{10}$) and one or more triple bonds. Examples of alkynyl and alkynylene include, but are not limited to, ethynyl, 1-propynyl, 1- and 2-butynyl, and 1-methyl-2-butynyl. The term "alkoxy" refers to an —O-alkyl radical. Examples of alkoxy include, but are not limited to, methoxy, ethoxy, n-propoxy, isopropoxy, n-butoxy, isobutoxy, sec-butoxy, and tert-butoxy.

The terms "cycloalkyl" and "cycloalkylene" respectively refer to a monovalent and a bivalent saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cyclohexylene, cycloheptyl, and cyclooctyl. The terms "cycloalkenyl" and "cycloalkenylene" respectively refer to a monovalent and a bivalent non-aromatic hydrocarbon ring system having 3 to 30 carbons (e.g., $C_3$-$C_{12}$) and one or more double bonds. Examples include cyclopentenyl, cyclohexenyl, and cycloheptenyl. The terms "heterocycloalkyl" and "heterocycloalkylene" respectively refer to a monovalent and a bivalent nonaromatic 5-8 membered monocyclic, 8-12 membered bicyclic, or 11-14 membered tricyclic ring system having one or more heteroatoms (such as O, N, S, or Se). Examples of heterocycloalkyl and heterocycloalkylene groups include, but are not limited to, piperazinyl, pyrrolidinyl, dioxanyl, morpholinyl, and tetrahydrofuranyl. The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds. The term "heterocycloalkenylene" refers to a bivalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, 14-carbon tricyclic aromatic ring system. Examples of aryl groups include, but are not limited to, phenyl, naphthyl, and anthracenyl. The term "arylene" refers to a bivalent 6-carbon monocyclic, 10-carbon bicyclic, 14-carbon tricyclic aromatic ring system. The term "aryloxyl" refers to an —O-aryl. The term "arylamino" refers to an —N(R)-aryl in which R can be H, alkyl, alkenyl, alkynyl, cycloalkyl, cycloalkenyl, heterocycloalkyl, heterocycloalkenyl, aryl, or heteroaryl. The term "heteroaryl" refers to a monvalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, and thiazolyl. The term "heteroarylene" refers to a bivalent aromatic 5-8 membered monocyclic, 8-12 membered bicyclic, or 11-14 membered tricyclic ring system having one or more heteroatoms (such as O, N, S, or Se).

Alkyl, alkenyl, alkynyl, cycloalkyl, heterocycloalkyl, cycloalkenyl, heterocycloalkenyl, aryl, heteroaryl, alkylene, alkenylene, alkynylene, cycloalkylene, heterocycloalkylene, cycloalkenylene, heterocycloalkenylene, arylene, and heteroarylene mentioned above include both substituted and unsubstituted moieties. Possible substituents on cycloalkyl, cycloalkenyl, heterocycloalkyl, heterocycloalkenyl, cycloalkylene, heterocycloalkylene, cycloalkenylene, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxy, halo, oxo (O=), thioxo (S=), thio, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, alkynyl, alkylene, alkenylene, or alkynylene include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Shown below are exemplary thiourea compounds that can be used to practice the method of the invention:

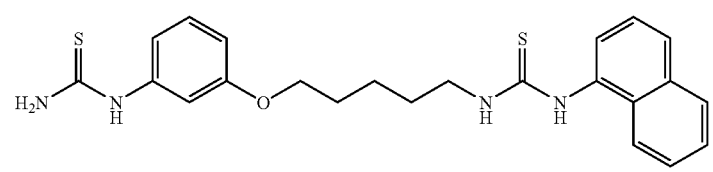

Compound 1

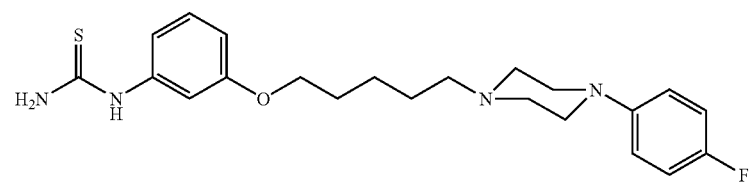

Compound 2

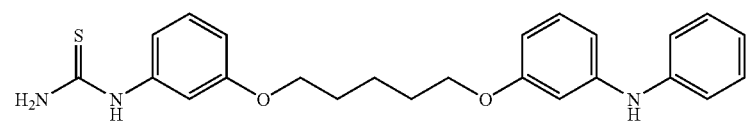

Compound 3

Compound 4

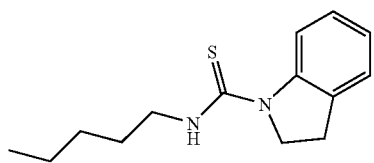

Compound 5

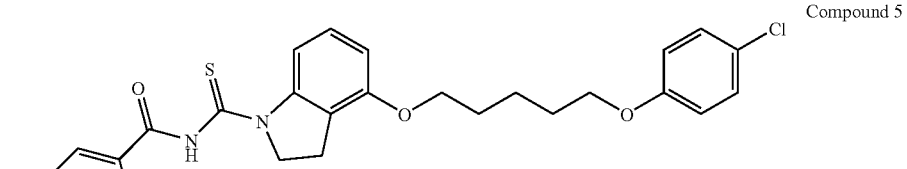

Compound 6

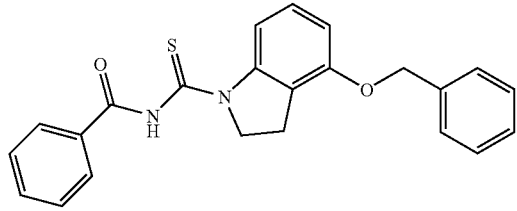

Other thiourea compounds disclosed in U.S. patent application Ser. Nos. 11/839,326 and 11/839,346, both filed on Aug. 15, 2007, U.S. Provisional Applications 60/910,892 filed on Apr. 11, 2007, 60/942,808 filed on Jun. 8, 2007, and 61/019,663 filed on Jan. 8, 2008, can also be used to practice the method of this invention. Methods of synthesizing various thiourea compounds were also disclosed in the above patent applications.

The thiourea compounds described above include the compounds themselves, as well as their salts, their solvates, and their prodrugs, if applicable. A salt, for example, can be formed between an anion and a positively charged group (e.g., amino) on a thiourea compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a thiourea compound. Suitable cations include sodium ion, potassium ion, magnesium ion, calcium ion, and an ammonium cation such as tetramethylammonium ion. The thiourea compounds also include those salts containing quaternary nitrogen atoms. Examples of prodrugs include esters and other pharmaceutically acceptable derivatives, which, upon administration to a subject, are capable of providing active thiourea compounds.

Also within the scope of this invention is a pharmaceutical composition containing one or more of the above-described thiourea compounds for use in treating neurodegenerative disorders, as well as this therapeutic use and use of the compounds for the manufacture of a medicament for treating neurodegenerative disorders.

The details of one or more embodiments of the invention are set forth in the description below. Other features, objects, and advantages of the invention will be apparent from the description and from the claims

DETAILED DESCRIPTION

This invention relates to use of one or more thiourea compounds described in the summary section above for treating a neurodegenerative disorder.

The thiourea compounds can be prepared by conventional chemical transformations (including protecting group methodologies), e.g., those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof. Schemes 1-7 below show transformations for synthesizing certain thiourea compounds of formula (I) or (II). $A_1$ and $A_2$ are defined above.

The route shown in Scheme 1 exemplifies synthesis of the thiourea compounds of formula (I) in which Z is NHC(O)NH or NH(CS)NH. O and S are both denoted as W in this scheme. Dibromo alkyl i is reacted with a nitro- and hydroxy-substituted aryl or heteroaryl (e.g., 3-nitrophenol) in the presence of potassium carbonate in N-methylpyrrolidone (NMP) to form an alkoxy-containing compound ii, which is subsequently treated with sodium azide to afford azide compound iii. Reduction of the azide compound leads to amine compound iv, which is then coupled with aryl isocyanate (or isothiocyanate) to form a urea (or thiourea) intermediate v. Subsequent reduction of the nitro group produces amine compound vi, which is then reacted with thiocarbonyl diimidazole (TCDI), followed by treatment with 25% aqueous ammonia solution, to afford thiourea compound vii (e.g., compound 1).

Scheme 1

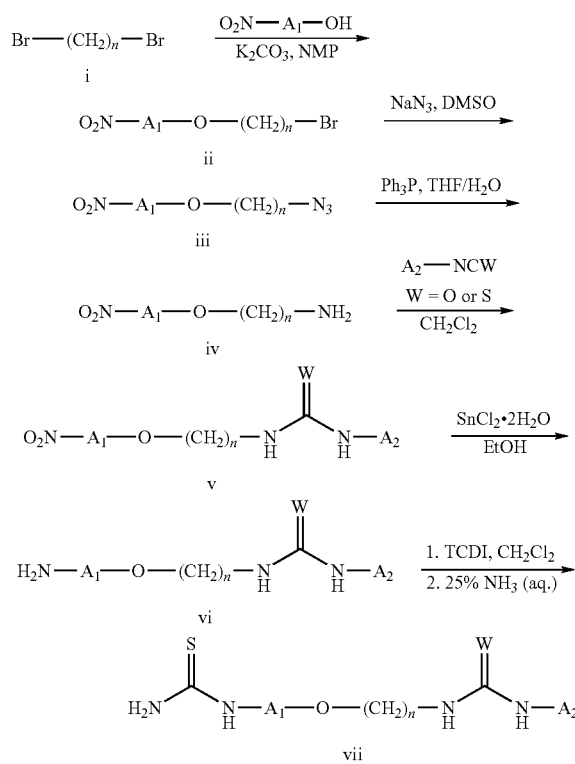

The route shown in Scheme 2 exemplifies synthesis of the thiourea compounds of formula (I) in which Z is —NHSO₂—, —NHC(O)—, or —NHC(O)O—. Amine compound iv is coupled with acyl chloride (sulfonyl chloride, or chloroformate) to provide compound viii. Reduction of compound viii with SnCl₂ produces amine compound ix, which is subsequently reacted with TCDI to afford thiourea compound x.

Scheme 2

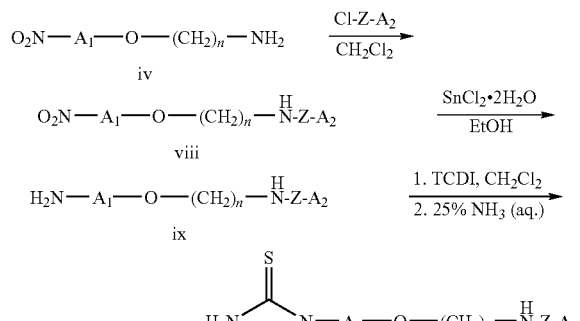

Z = CO, C(=O)O, or SO₂

The route shown in Scheme 3 exemplifies synthesis of the thiourea compounds of formula (I) in which Z is piperazinyl. Coupling bromo compound ii with piperazine derivative affords compound xi, which is subsequently converted to amine xii by reducing its nitro group. Amine xii compound is then reacted with TCDI to afford thiourea compound x (e.g., compound 2).

Scheme 3

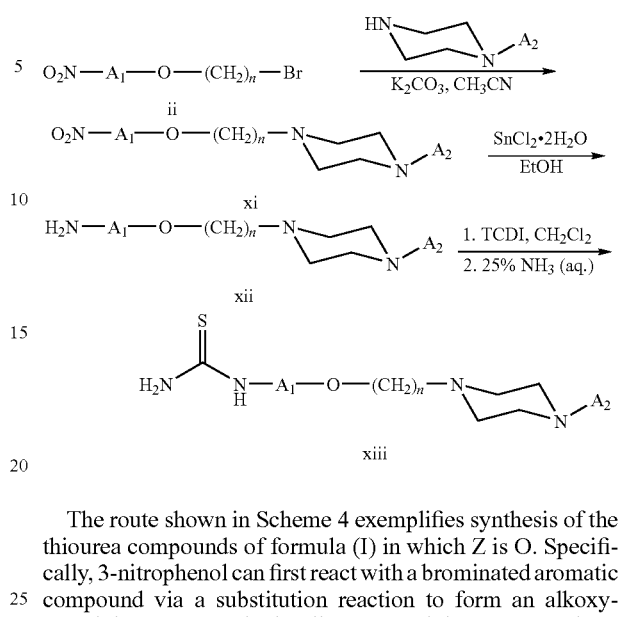

The route shown in Scheme 4 exemplifies synthesis of the thiourea compounds of formula (I) in which Z is O. Specifically, 3-nitrophenol can first react with a brominated aromatic compound via a substitution reaction to form an alkoxy-containing compound. The alkoxy-containing compound can then be reduced (e.g., by hydrogen or tin chloride) to convert the nitro group to an amino group. The compound thus formed can then be treated with TCDI and a base (e.g., ammonia) to form a thiourea compound for practicing the invention (e.g., compound 3).

Scheme 4

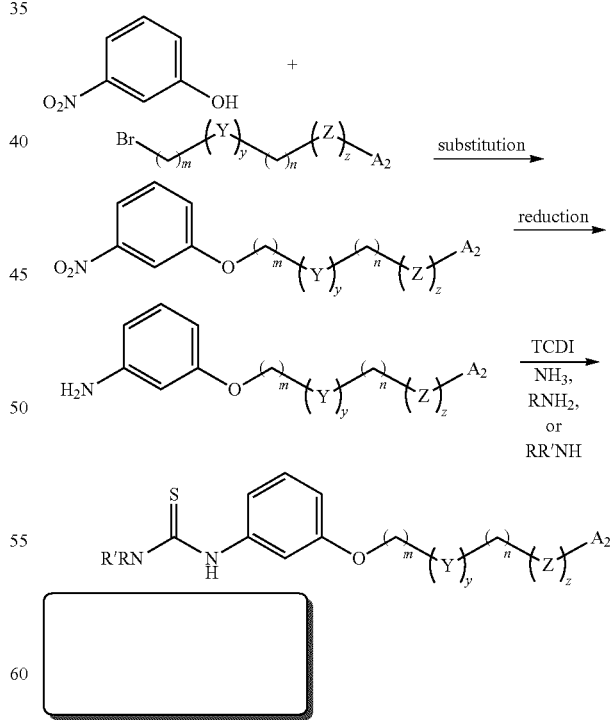

The routes shown in Scheme 5 exemplify synthesis of the thiourea compounds of formula (I) in which R₃ and the nitrogen atom to which it is bonded, together with A₁, are a N-containing bicyclic moiety. Specifically, The N-containing bicyclic moiety can be prepared by cyclization or by reduction of an aromatic bicyclic ring. The thiourea moiety of the thiourea compounds can be prepared by reacting the N-containing bicyclic moiety with TCDI followed by treatment of amine or ammonium, or by reacting the N-containing bucyclic moiety with an isothiocyanate (—NCS) compound form the thiourea compounds for practicing the invention (e.g., compounds 4-6).

The route shown in Scheme 6 exemplifies synthesis of certain thiourea compounds of formula (II). Specifically, certain thiourea compounds can be prepared from a monoamino aromatic compound. For example, as shown in Scheme 6 below, a monoamino aromatic compound can react with thiocarbonyl diimidazole, followed by ammonia or a primary amine, to form a thiourea compound of formula (II).

Scheme 5

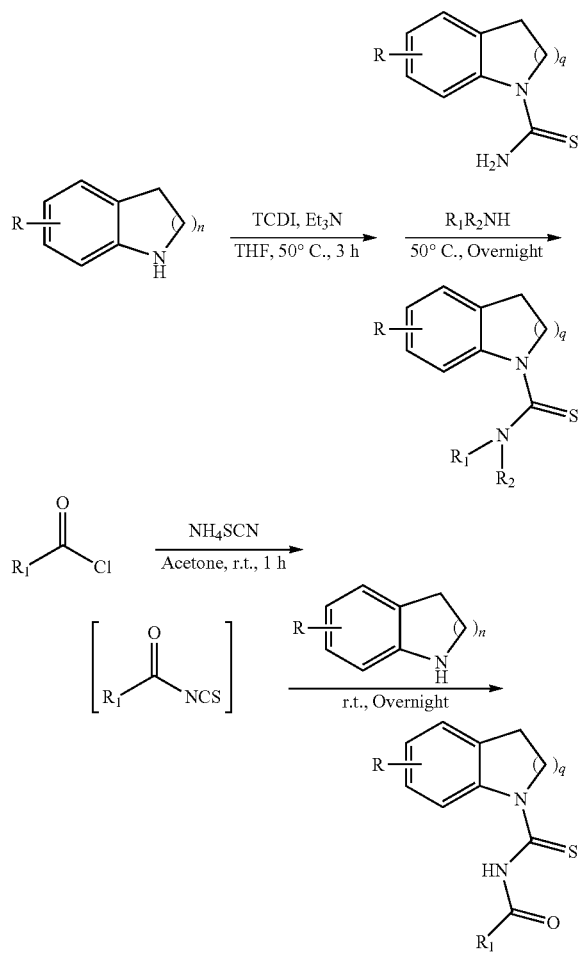

Scheme 6

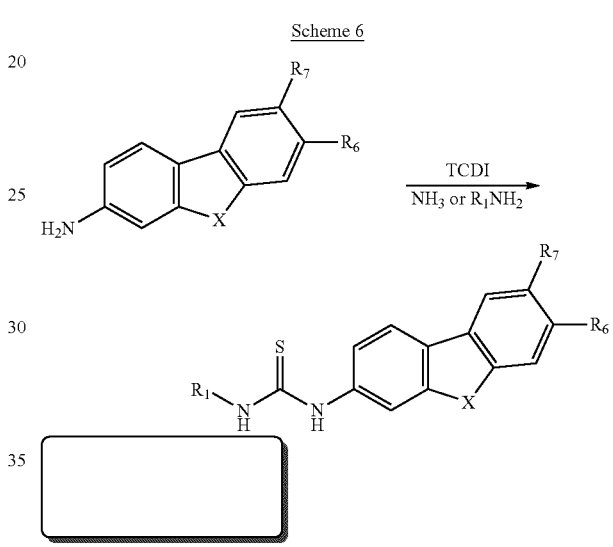

The route shown in Scheme 7 also exemplifies synthesis of certain thiourea compounds of formula (II). Specifically, certain other thiourea compounds can be prepared from a diamino aromatic compound. For example, as shown in Scheme 7 below, one amino group on 9H-fluorene-2,7-diamine can first be protected with a tert-butyloxycarbonyl (Boc) protecting group. The other amino group 9H-fluorene-2,7-diamine can then react with a halo-containing compound to form either a compound containing a secondary amino group or a compound containing a tertiary amino group. The compound thus formed can be deprotected (e.g., by reacting with trifluoroacetic acid) and then treated with thiocarbonyl diimidazole and a base to form a thiourea compound of formula (II).

Scheme 7

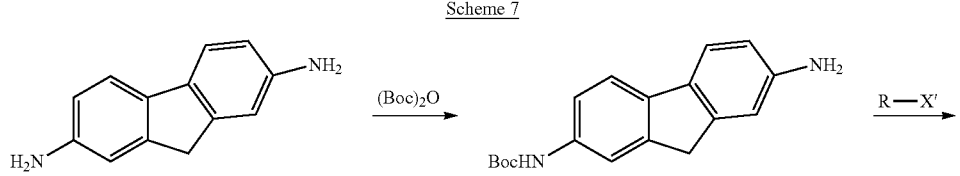

-continued

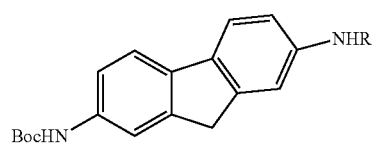 + 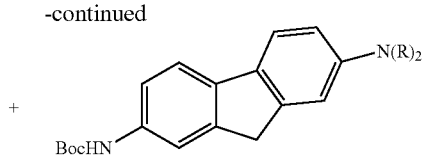

↓ TFA          ↓ TFA

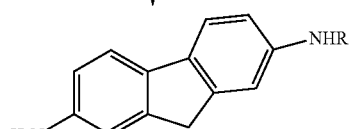          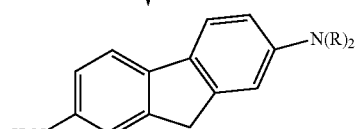

base ↓ TCDI   base ↓ TCDI

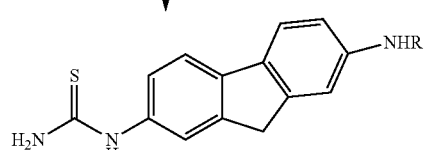          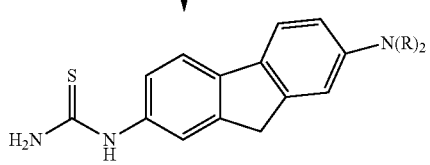

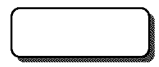

More methods for obtaining various thiourea compounds can be found in U.S. patent application Ser. Nos. 11/839,326 and 11/839,346, and U.S. Provisional Applications 60/910,892, 60/942,808, and 61/019,663, supra.

A thiourea compound thus synthesized can be further purified by flash column chromatography, high performance liquid chromatography, crystallization, or any other suitable methods.

The thiourea compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Also within the scope of this invention is a pharmaceutical composition contains an effective amount of at least one thiourea compound described above and a pharmaceutical acceptable carrier. This invention also covers a method of administering an effective amount of one or more thiourea compounds to reduce microglia-mediated neuro-inflammation and/or enhancing phagocytosis of Aβ and to treat neurodegenerative disorders such as AD and PD. Effective doses will vary, as recognized by those skilled in the art, depending on the route of administration, excipient usage, and the possibility of co-usage with other therapeutic treatment.

To practice the method of the present invention, a composition having one or more thiourea compounds can be administered parenterally, orally, nasally, rectally, topically, buccally, vaginally, or via an implanted reservoir. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A thiourea compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, one or more solubilizing agents, which form more soluble complexes with the thiourea compounds, can be utilized as pharmaceutical carriers for delivery of the active thiourea compounds. Examples of other carriers include colloidal silicon dioxide, magnesium stearate, sodium lauryl sulfate, and D&C Yellow #10.

Suitable in vitro assays can be used to preliminarily evaluate the efficacy of the thiourea compounds in reducing microglia-mediated neuro-inflammation and enhancing phagocytosis of Aβ. See Examples 7 and 8 below. The compounds can further be examined for their efficacy in treating a neurodegenerative disorder. For example, a compound can be tested in an AD or PD animal model (e.g., APP transgenic mice or MPTP-treated mice) and clinical trials. Its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications and patent applications cited herein are hereby incorporated by reference in their entirety.

EXAMPLE 1

Synthesis of 1-naphthalen-1-yl-3-[5-(3-thioureido-phenoxy)-pentyl]-thiourea (compound 1)

To a stirred solution of 3-nitrophenol (4.17 g, 30.0 mmol) and 1,5-dibromo-pentane (7.59 g, 33.0 mmol) in N-methylpyrolidinone (100 mL) was added potassium carbonate (6.21 g, 45.0 mmol), and the resulting mixture was stirred at 90° C. for 6 hours. The reaction mixture was quenched with water (30 mL) followed by extraction with ethyl acetate (30 mL×3). The combined organic layers were washed with brine and then concentrated under vacuum. The residue was purified by silica gel column chromatography to give 1-(5-bromo-pentyloxy)-3-nitro-benzene (5.10 g, 17.7 mmol, 59%) as a yellow liquid.

The resulting yellow liquid (3.60 g, 12.5 mmol) was dissolved in DMSO (20 mL). Sodium azide (1.22 g, 18.7 mmol) was slowly added. The reaction mixture was stirred overnight at room temperature and then quenched with water (30 mL) followed by extraction with ether (30 mL×3). The combined organic layers were washed with brine and then concentrated under vacuum. The residue was purified by silica gel column chromatography to give 1-(5-azido-pentyloxy)-3-nitro-benzene (3.12 g, 12.5 mmol, 99%) as a yellow liquid.

To a solution of 1-(5-azido-pentyloxy)-3-nitro-benzene (3.12 g, 12.5 mmol) in 50 mL THF and 1 mL $H_2O$ was added triphenylphosphine (3.27 g, 12.5 mmol). The reaction mixture was stirred at room temperature for 48 hours and then was partitioned with ethyl acetate and water. The aqueous solution was extracted with ethyl acetate (3×50 mL). The combined organic phases were washed with brine, dried over $MgSO_4$, and concentrated to give a yellow liquid, which was purified by silica gel column chromatography to give 5-(3-nitro-phenoxy)-pentylamine (2.75 g, 12.3 mmol, 98%) as a yellow liquid.

To a solution of 5-(3-nitro-phenoxy)-pentylamine (867 mg, 3.87 mmol) in dichloromethane (5 mL) was added 1-naphthyl isothiocyanate (788 mg, 4.26 mmol) at room temperature. The reaction mixture was stirred at room temperature overnight. After removal of the solvent, the residue was purified by silica gel column chromatography to give 1-naphthalen-1-yl-3-[5-(3-nitro-phenoxy)-pentyl]-thiourea (1.3 g, 3.18 mmol, 82%) as a yellow gel.

The yellow gel (1.3 g, 3.18 mmol) was dissolved in 30 mL ethanol. To this solution was added Tin (II) chloride dihydrate (4.05 g, 15.9 mmol). The reaction mixture was stirred at 70° C. for 6 hours. Upon cooling, saturated aqueous sodium bicarbonate solution was added to adjust the pH value to 7. The solution was then extracted with ethyl acetate (3×50 mL). The combined organic phases were washed with brine, dried over $MgSO_4$, and concentrated to give a yellow gel, which was purified by silica gel column chromatography eluting with ethyl acetate and n-hexane to give 1-[5-(3-amino-phenoxy)-pentyl]-3-naphthalen-1-yl-thiourea (1.2 g, 3.17 mmol, 99%) as a light yellow solid.

1-[5-(3-amino-phenoxy)-pentyl]-3-naphthalen-1-yl-thiourea (1.76 g, 4.65 mmol) was mixed with thiocarbonyl diimidazole (993 mg, 5.58 mmol) in dichloromethane (25 mL) and was stirred at room temperature for 2 hours. 25% aqueous ammonia solution (3 mL) was added and the reaction mixture was stirred at room temperature overnight. After removal of the solvent, the residue was purified by silica gel column chromatography eluting with ethyl acetate and n-hexane to give Compound 1 (1.7 g, 3.88 mmol, 83%) as a white solid. MS (EI): m/z 439 (M+H).

EXAMPLE 2

Synthesis of (3-{5-[4-(4-fluoro-phenyl)-piperazin-1-yl]-pentyloxy}-phenyl)-thiourea (compound 2)

To a stirred solution of 1-(5-bromo-pentyloxy)-3-nitrobenzene (432 mg, 1.5 mmol) and 1-(4-fluoro-phenyl)-piperazine (297 mg, 1.65 mmol) in acetonitrile (5 mL) was added potassium carbonate (414 mg, 3.0 mmol). After refluxed for 6 hours, the reaction mixture was quenched with water (10 mL) followed by extraction with ethyl acetate (10 mL×3). The combined organic layers were washed with brine and then concentrated under vacuum. The resulting residue was purified by silica gel column chromatography to give 1-(4-fluoro-phenyl)-4-[5-(3-nitro-phenoxy)-pentyl]-piperazine (549 mg, 1.42 mmol, 94%) as a yellow solid.

The obtained compound (549 mg, 1.42 mmol) was dissolved in 5 mL ethanol. Tin (II) chloride dihydrate (1.81 g, 7.08 mmol) was then added. The reaction mixture was stirred at 70° C. for 3 hours. Upon cooling, saturated aqueous sodium bicarbonate solution was added to adjust the mixture's pH value to 7. The solution was extracted with ethyl acetate (3×10 mL), and the combined organic phases were washed with brine, dried over $MgSO_4$, and concentrated to give a white solid, which was purified by silica gel column chromatography eluting with ethyl acetate-n-hexane to give 3-{5-[4-(4-fluoro-phenyl)-piperazin-1-yl]-pentyloxy}-phenylamine (500 mg, 1.40 mmol, 99%) as a white solid.

A solution of 3-{5-[4-(4-fluoro-phenyl)-piperazin-1-yl]-pentyloxy}-phenylamine (500 mg, 1.40 mmol) and thiocarbonyl diimidazole (299 mg, 1.68 mmol) in dichloromethane (4 mL) was stirred at room temperature for 2 hours. 25% aqueous ammonia solution (2 mL) was added. The reaction mixture was stirred at room temperature overnight and then the solvent was removed. The residue was purified by silica gel column chromatography eluting with ethyl acetate and n-hexane to give (3-{5-[4-(4-fluoro-phenyl)-piperazin-1-yl]-pentyloxy}-phenyl)-thiourea (Compound 19) (425 mg, 1.02 mmol, 73%) as a white solid. MS (EI): m/z 417 (M+H).

EXAMPLE 3

Synthesis of {3-[5-(3-Phenylamino-phenoxy)-pentyloxy]-phenyl}-thiourea (compound 3)

Compound 3 was prepared in a manner similar to that outlined in Scheme 4.
EI-MS (M+1): 422.

EXAMPLES 4-6

Synthesis of 2,3-Dihydro-indole-1-carbothioic acid pentylamide (compound 4), N-{4-[5-(4-chloro-phenoxy)-pentyloxy]-2,3-dihydro-indole-1-carbothioyl}-4-cyano-benzamide (compound 5), and N-(5-benzyloxy-2,3-dihydro-indole-1-carbothioyl)-benzamide (compound 6)

Compound 4-6 were prepared in a manner similar to that outlined in Scheme 5.
EI-MS (M+1): 249 (compound 4), 520 (compound 5), 389 (compound 6).

EXAMPLE 7

Enhancement of Microglial Aβ Clearance and Phagocytosis In Vitro

Compounds were evaluated for their efficacy in enhancing microglial phagocytosis of Aβ (or Aβ clearance). Microglia were pretreated with a test compound at concentration of 1 μM for 1 hr followed by 24 hr treatment of FITC-labeled Aβ1-42 (100 nM). Lipopolysaccharide (LPS) at 10 ng/mL was added as a positive control, which is known to increase Aβ uptake. The culture medium was subjected to Western blotting for evaluating residual Aβ left in the medium. The mean values of fluorescent intensity measured by flow cytometer were compared between cells pretreated with the test compound and the ones in non-treated controls.

Twenty thiourea compounds, including Compounds 1-6, were tested. Unexpectedly, treatment with Compounds 1-6 at 1 μM for 24 hr lowered Aβ level to approximately 45%-90% of that in non-treated control; Compound 1 at 10, 20, and 50 μM increased Aβ uptake by approximately 29% (n=6, p<0.001), 44% (n=6, p<0.001), and 128% (n=6, p<0.001), respectively, as compared to the controls.

EXAMPLE 8

Anti-Inflammatory Activity

Compounds were evaluated for their efficacy in suppressing microglial immune activation by measuring their potency against LPS-induced expression of iNOS and COX-2 and IL-6 secretion. Microglia and Raw 264.7 cells (a microglia-like cell line) were pretreated with a test compound at various doses for 1 hr followed by 24 hr treatment of LPS (10 ng/ml). Cell lysates were subjected to Western blotting for iNOS and COX-2 evaluation. IL-6 secretion was measured from resulting culture medium by ELISA.

Statistical analysis showed cells pretreated with compound 1 showed a significant suppression in LPS-induced iNOS and COX-2 expression in a dose dependent manner, while the house keeping protein, β-actin, remained unchanged. In addition, compound 1 inhibited LPS-induced IL-6 secretion by microglia in a dose dependent manner, which is beneficial for retaining hippocampal functions during neuro-inflammation. Effective doses of compound 1 to show at least 50% suppression (i.e., $IC_{50}$) for iNOS, COX-2, and IL-6 are 1 μM, 50 μM and, 20 μM, respectively.

EXAMPLE 9

Neuro-Protection Against LPS Toxicity

Compounds were evaluated for their efficacy in suppressing microglia-mediated neurotoxicity. Hippocampal organotypic cultures were established to serve as an ex vivo model for evaluation of hippocampal functions. Pre-treatment of the cultures with a test compound was followed by addition of LPS (10 ng/mL) for 24 hr. Hippocampal tissues were harvested and subjected to Western blotting for measuring synaptophysin and post synaptic density protein (PSD)95 levels, the indications for neuronal synatic functions.

Unexpectedly, pre-treatment with compound 1 prevented LPS-induced reduction of synaptophysin and PSD95 levels in hippocampal organotypic cultures, which indicated that compound 1 may be neuroprotective against LPS toxicity by suppressing microglial activation ex vivo.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A method for treating Alzheimer's disease, comprising administering to a subject in need thereof an effective amount of 1-naphthalen-1-yl-3-[5-(3-thioureido-phenoxy)-pentyl]-thiourea.
2. A method for treating Parkinson's disease, comprising administering to a subject in need thereof an effective amount of 1-naphthalen-1-yl-3-[5-(3-thioureido-phenoxy)-pentyl]-thiourea.

* * * * *